US012788632B2

(12) United States Patent
Deng et al.

(10) Patent No.: US 12,788,632 B2
(45) Date of Patent: Nov. 10, 2026

(54) ULTRASONIC EMULSIFIER

(71) Applicant: MICROPORT VISIONPOWER MEDTECH (SHANGHAI) CO., LTD., Shanghai (CN)

(72) Inventors: Weixin Deng, Shanghai (CN); Zhaohua Chang, Shanghai (CN); Ruishen Hu, Shanghai (CN); Yiqiu Wen, Shanghai (CN); Qiou Chen, Shanghai (CN); Jie Zhang, Shanghai (CN); Qiyi Luo, Shanghai (CN)

(73) Assignee: MICROPORT VISIONPOWER MEDTECH (SHANGHAI) CO., LTD., Shanghai (CN)

( * ) Notice: Subject to any disclaimer, the term of this patent is extended or adjusted under 35 U.S.C. 154(b) by 453 days.

(21) Appl. No.: 18/558,145

(22) PCT Filed: Apr. 2, 2022

(86) PCT No.: PCT/CN2022/085071

§ 371 (c)(1),
(2) Date: Oct. 30, 2023

(87) PCT Pub. No.: WO2022/228044

PCT Pub. Date: Nov. 3, 2022

(65) Prior Publication Data

US 2024/0216171 A1 Jul. 4, 2024

(30) Foreign Application Priority Data

Apr. 30, 2021 (CN) ........................ 202110485651.4

(51) Int. Cl.
*A61F 9/007* (2006.01)

(52) U.S. Cl.
CPC .......... *A61F 9/00745* (2013.01); *A61F 9/007* (2013.01)

(58) Field of Classification Search
CPC ............................ A61F 9/00745; A61F 9/007
See application file for complete search history.

(56) References Cited

U.S. PATENT DOCUMENTS

2008/0114312 A1* 5/2008 Muri .................... F04B 49/065 604/35
2009/0149840 A1 6/2009 Kurtz
(Continued)

FOREIGN PATENT DOCUMENTS

CN 101632610 A 1/2010
CN 103917637 A 7/2014
(Continued)

*Primary Examiner* — Tasnim Mehjabin Ahmed
(74) *Attorney, Agent, or Firm* — MUNCY, GEISSLER, OLDS & LOWE, P.C.

(57) ABSTRACT

An ultrasonic emulsifier includes an emulsifier body (201), on which there are provided: an irrigation module (202) for dispensing a liquid into an eye, the liquid containing targeted microbubbles (401) for acting on a lens of the eye; an ultrasound module (203) for producing ultrasound waves for acting on the eye and enabling the targeted microbubbles (401) to act on the lens (101) of the eye; and a suction module for aspirating the dispensed liquid and/or the broken-down lens (101) from the eye. This ultrasonic emulsifier can overcome the problem of possible damage to other parts of the eye during cataract surgery and consequent complications.

12 Claims, 6 Drawing Sheets

(56) References Cited

U.S. PATENT DOCUMENTS

| | | | | |
|---|---|---|---|---|
| 2013/0211395 | A1* | 8/2013 | Schwartz | A61F 9/00781 606/28 |
| 2020/0214890 | A1* | 7/2020 | Grubbs | A61F 9/00745 |

FOREIGN PATENT DOCUMENTS

| | | | |
|---|---|---|---|
| CN | 108593783 | A | 9/2018 |
| CN | 208464423 | U | 2/2019 |

* cited by examiner

ULTRASONIC EMULSIFIER

TECHNICAL FIELD

The present invention relates to the field of medical equipment and, in particular, to an ultrasonic emulsifier.

BACKGROUND

Our eyes allow us to see because light travels through the clear part of the cornea and is then focused by the crystalline lens as an image on the retina. The quality of vision is contingent upon various factors including size of the eyes and transparency of the cornea and lens. The lens' transparency may deteriorate due to age and pathological conditions, reducing light that can reach the retina and leading to hazy vision or even blindness. These conditions are known as cataracts. FIG. 1 schematically illustrates the structure of the human eye 100, which is composed of the lens 101, vitreous body 102, anterior chamber 103, sclera 104, iris 105, cornea 106, optic nerve 107 and retina 108. The lens 101 is normally transparent, and light can travel through it and some refracting medium and reach the retina 108, allowing the eye to see objects clearly. In simple terms, a cataract is a condition with haziness, reduced transparency, a color change or the like, which occurs to the lens 101 due to some pathological causes and impedes the penetration of light into the eye and eventually affects vision. Clinically, cataracts are generally divided into age-related, congenital, traumatic, metabolic (e.g. diabetic) and secondary (e.g., develop as a result of glaucoma). Age-related cataracts are most common, and congenital cataracts require parents' attention because the incidence of this disease is about 0.5% among newborn babies and is the second reason for child blindness.

So far, there are no drugs with proven clinical benefits against cataracts. Currently, phacoemulsification is a recognized treatment for this disease, which involves surgical replacement of the defective lens with an artificial intraocular lens (IOL).

Phacoemulsification allows a surgeon to surgically treat a cataract through a tiny incision made in the cornea. During the surgical treatment, ultrasound energy is delivered at a high frequency (typically in the range of from 20 kHz to 60 kHz) to break down or emulsify the lens nucleus of concern, followed by aspiration of the resulting slurry and implantation of an artificial IOL.

FIG. 2 shows a conventional ultrasonic emulsifier for cataract treatment, which is applicable to lensectomy and IOL implantation. This apparatus can be used to emulsify a crystalline lens within an eyeball, remove the resulting slurry and replace the removed lens with a balanced salt solution. This conventional apparatus emulsifies the lens by breaking down the diseased nucleus with high-frequency ultrasound energy, then removing the material of the broken down or emulsified nucleus and finally implanting an artificial IOL. However, the high-frequency ultrasound energy used may cause damage to the vulnerable eye tissue. In particular, harder cataracts require higher ultrasound energy, which is more likely to cause damage to other parts of the eye and hence various possible complications.

Since Charles D. Kelman introduced the concept of phacoemulsification for surgical cataract treatment in 1967, phacoemulsification technology has been advancing, and various approaches for more efficient energy delivery and ultrasonic power adjustment have been developed. Use of less ultrasound energy means, for example, fewer complications and better surgical outcomes. Moreover, innovations have been made to the mode of ultrasonic vibration used in this type of surgery. For example, torsional and elliptical modes have been developed in addition to the conventional longitudinal mode. These allow lateral and elliptical motion of the tip of a phacoemulsification needle, avoiding an excessive longitudinal stroke of the tip which may cause damage to the eye.

Although these advancements allow efficient delivery of ultrasound energy to a cataract nucleus, current phacoemulsification still relies on the insertion of a needle tip or probe into the eye for releasing high-frequency ultrasound energy for breaking down a cataract nucleus. In particular, the breakdown of a harder cataract nucleus requires the use of ultrasound energy delivered at a higher frequency, which is likely to cause damage to the vulnerable surrounding eye tissue. Therefore, although the existing phacoemulsification approach is able to effectively separate and emulsify the lens, it is associated with considerable safety issues. According to preliminary statistics, about 1% to 4% of patients who received phacoemulsification have reported complications that affect vision. In addition, although phacoemulsification procedures are relatively simple procedures in the field of ophthalmology, even a dexterous surgeon may perhaps unnecessarily use excessive energy during a phacoemulsification procedure, which can lead to loss of corneal endothelial cells and consequent edema or other sequelae. When this happens, a longer healing time may be necessary, or even an irreversible corneal nebula requiring surgical treatment may develop. Therefore, in the United States, only those having at least three years of experience as a resident ophthalmologist are allowed to receive training for cataract surgery. In China, due to equipment and other limitations, even more stringent requirements are placed on such training.

Apart from the above-discussed safety issues, each single ultrasonic emulsifier can incur a significant expenditure including both one-time cost of the apparatus itself and continuous expenditure of associated disposable consumables. Therefore, there is a need for a novel phacoemulsification paradigm, which can serve as a cheaper and safer alternative to the conventional high-energy approach while providing comparable cataract removal performance.

SUMMARY OF THE INVENTION

It is an objective of the present invention to provide an ultrasonic emulsifier which overcomes the problem of possible damage to other part of the eye during cataract surgery and consequent possible complications associated with conventional ultrasonic emulsifiers.

To this end, the present invention provides an ultrasonic emulsifier including an emulsifier body, on which there are provided: an irrigation module for dispensing a liquid into an eye, the liquid containing targeted microbubbles for acting on a lens of the eye; an ultrasound module for producing ultrasound waves for acting on the eye and enabling the targeted microbubbles to act on the lens of the eye; and a suction module for aspirating the dispensed liquid and/or the broken-down lens from the eye.

Additionally, the irrigation module may include a gravitational irrigation module including a support rod and an irrigation container, the support rod disposed on the emulsifier body so as to extend outwardly from the emulsifier body, the irrigation container disposed at a top end of the support rod away from the emulsifier body.

Additionally, the support rod may have an adjustable length.

Additionally, the irrigation module may further include an irrigation handle configured to dispense into the eye the liquid that contains the targeted microbubbles for acting on the lens of the eye.

Additionally, the irrigation module may further include an irrigation handle in communication with the gravitational irrigation module, wherein the gravitational irrigation module is configured to supply a balanced salt solution to the irrigation handle, and the irrigation handle is configured to suck the targeted microbubbles therein and dispense the targeted microbubbles into the eye.

Additionally, the suction module may include a suction handle for aspirating the dispensed liquid and/or the broken-down lens from the eye.

Additionally, the irrigation handle and the suction handle may be implemented as a single handpiece defining an irrigation passage and a suction passage, wherein the gravitational irrigation module is configured to supply the balanced salt solution to the irrigation passage of the handpiece; the irrigation passage of the handpiece is configured for suction of the targeted microbubbles that target and bind to the lens of the eye and for dispensing the targeted microbubbles into the eye; and the suction passage is configured for suction of the dispensed liquid and/or the broken-down lens from the eye.

Additionally, the ultrasonic emulsifier may further include a fluid management module connected to both the irrigation module and the suction module and configured for flow rate control of the irrigation module and the suction module.

Additionally, the fluid management module may include a fluid management module, a control pump, an irrigation valve, a sensing module and a fluid collection cassette, the irrigation module communicating with the fluid collection cassette through the irrigation valve; the suction module communicating with the fluid collection cassette through the control pump; the sensing module configured to collect pressure signals from the fluid collection cassette, the irrigation module and the suction module and provide them to the fluid management module, the fluid management module configured to determine an irrigation pressure of the irrigation module and/or a suction pressure of the suction module from the pressure signals from the sensing module and regulate operation of the control pump and the irrigation valve based on the irrigation pressure and/or the suction pressure, the control pump configured to produce a negative pressure for adjusting a suction flow rate and the suction pressure of the suction module, the irrigation valve configured to adjust an irrigation flow rate and the irrigation pressure of the irrigation module.

Additionally, the irrigation module may include the gravitational irrigation module and the irrigation handle, wherein the gravitational irrigation module communicates with the irrigation handle through the irrigation valve and the fluid collection cassette; the suction module includes the suction handle which communicates with the fluid collection cassette through a pipe and the control pump; the gravitational irrigation module is configured to supply the balanced salt solution to the irrigation handle through the irrigation valve and the fluid collection cassette; the irrigation handle is configured to suck therein the targeted microbubbles for acting on the lens of the eye and dispense the targeted microbubbles into the eye; and the suction handle is configured to aspirate the dispensed liquid and/or the broken-down lens from the eye.

Additionally, the irrigation handle and the suction handle may be implemented as the single handpiece defining the irrigation passage and the suction passage, wherein the gravitational irrigation module communicates with the irrigation passage of the handpiece through the irrigation valve and the fluid collection cassette, and the suction passage of the handpiece communicates with the fluid collection cassette through a pipe and the control pump.

Additionally, the ultrasound module may include a focusing ultrasound transducer for providing focused ultrasound energy for acting on the eye.

Additionally, the focusing ultrasound transducer may include a plurality of piezoelectric elements, a carrier and an excitation component, the excitation component configured to excite the piezoelectric elements to cause them to generate ultrasound waves, the piezoelectric elements arranged on the carrier into an arc so that the ultrasound waves that they produce converge to provide the focused ultrasound energy.

Additionally, the focusing ultrasound transducer may further include a housing with an opening, wherein the carrier is arc-shaped and mounted in and aligned with the opening of the housing; the piezoelectric elements are spaced apart across an inner surface and/or an outer surface of the arc-shaped carrier; and each of the piezoelectric elements is electrically connected at one end to the arc-shaped carrier and the other ends of the piezoelectric elements are electrically connected together.

Additionally, negative poles of the piezoelectric elements may be grounded and positive poles thereof may be electrically connected to the excitation component.

Additionally, the excitation component may include a trigger module and a high-voltage pulse generator, wherein the positive poles of the piezoelectric elements are electrically connected to the high-voltage pulse generator, and the trigger module is connected to the high-voltage pulse generator.

Additionally, the ultrasonic emulsifier may further include a robotic arm coupled to the housing of the ultrasound module, the robotic arm configured to move the ultrasound module toward or away from the eye.

In summary, compared with the prior art, the ultrasonic emulsifier of the present invention has the advantages as follows:

It combines targeted microbubbles with ultrasonic cavitation by first dispensing the targeted microbubbles into a patient's eye and then activating the targeted microbubbles and inducing cavitation therein through the application of ultrasound energy. Energy generated from the cavitation breaks down the cataract nucleus in the diseased lens without causing damage to other tissue such as the lens capsule. Compared with direct breakdown of the cataract lens, less energy is required to activate the targeted microbubbles and induce cavitation therein. Therefore, compared with the conventional approach relying on direct ultrasonic breakdown of the cataract lens, the present invention can achieve lens breakdown using less ultrasound energy, resulting in less energy consumption and circumventing the use of excessive ultrasound energy which may cause damage to other parts of the eye and consequent complications of cataract surgery.

In addition, the ultrasound module of the present invention employs a focusing ultrasound transducer capable of producing pulsed ultrasound waves which can converge to gain the characteristics of strong directionality and less divergence. Compared with most of the conventional methods, which involve inserting an ultrasonic handpiece into the eye to apply ultrasonic energy thereto, the ultrasound module of the present invention entails a contactless approach allowing precise delivery of the focused ultrasound waves to the targeted microbubbles present around the eye's lens without inserting the ultrasound module into the eye, additionally reducing damage to other tissue of the eye. Moreover, because the directionality of the focused pulsed ultrasound waves is higher than that of the conventional phacoemulsification approach, coupled with their use in combination with the targeted microbubbles and the contactless approach, use of lower energy and a smaller incision is allowed, resulting in higher safety than the conventional methods.

Figure 1:
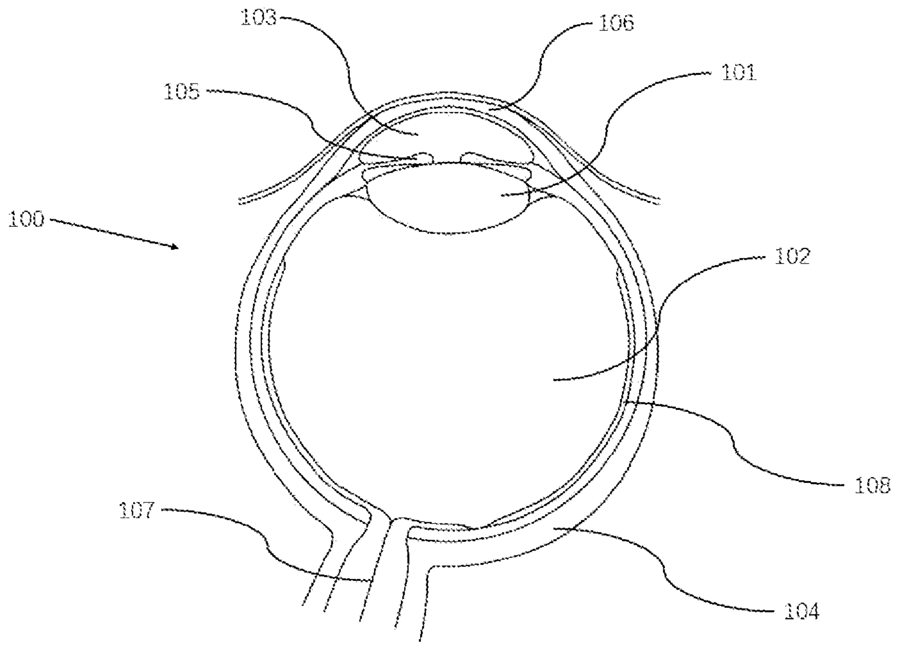
FIG. 1 schematically illustrates the structure of the human eye.
Figure 2:
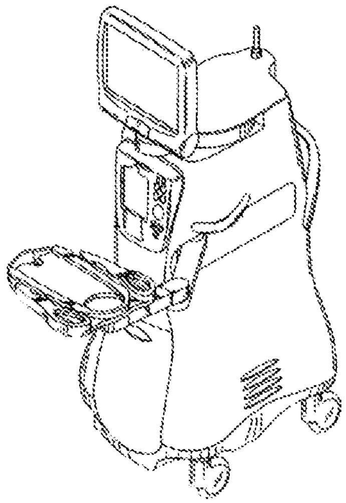
FIG. 2 is a schematic illustration of a cataract treatment apparatus.

100—eye; 101—lens; 102—vitreous body; 103—anterior chamber; 104—sclera; 105—iris; 106—cornea; 107—optic nerve; 108—retina; 201—emulsifier body; 202—irrigation module; 203—ultrasound module; 204—fluid management module; 2021—gravitational irrigation module; 20211—support rod; 2022—automated irrigation module; 2023—irrigation handle; 20231—syringe needle; 2030—excitation component; 2031—ultrasound wave; 2032—piezoelectric element; 2033—trigger module; 2034—high-voltage pulse generator; 2035—carrier; 2036—housing; 2037—filler; 2041—fluid management module; 2042—control pump; 2043—irrigation valve; 2044—fluid collection cassette; 401—targeted microbubble; 205—robotic arm; 206—vitrectomy module; 2071—first display screen; 2072—second display screen; 2073—foot pedal; 2074—surgical tray.

DETAILED DESCRIPTION

Ultrasonic emulsifiers proposed herein will be described below with respect to particular embodiments and with reference to the accompanying drawings. From the following description, advantages and features of the present invention will become more apparent.

It is to be noted that the figures are provided in a very simplified form not necessarily drawn to exact scale and for the only purpose of facilitating easy and clear description of the embodiments. In order that the objects, features and advantages of the present invention can be more apparent and readily understood, reference is to be made to the accompanying drawings. It would be recognized that architectural, proportional, dimensional and other details in the figures are presented only for the purpose of facilitating, in conjunction with the disclosure herein, the understanding and reading of those familiar with the art, rather than being intended to limit conditions under which the present invention can be implemented. Therefore, they are technically of no substantive significance, and any and all architectural modifications, proportional variations or dimensional changes that do not affect the benefits and objects of the present invention are considered to fall within the scope of the teachings herein.

In the description herein, it would be appreciated that the orientational and positional relationships described with the terms "central", "longitudinal", "transverse", "length", "width", "thickness", "upper", "lower", "front", "rear", "left", "right", "vertical", "horizontal", "top", "bottom", "inside", "outside", "axial", "radial", "circumferential", etc. are based on the orientations or positions shown in the accompanying drawings. They are intended merely to facilitate and simplify the explanation of the application and do not indicate or imply that the stated components or elements have to assume, or be constructed or operated in, particular orientations. Therefore, they are not to be construed as limiting the application.

As used herein, the terms "include," "including," or any other variations thereof are intended to cover a non-exclusive inclusion within a process, method, article, or apparatus that includes a list of elements including not only those elements but also those that are not explicitly listed, or other elements that are inherent to such processes, methods, goods, or equipment. In the case of no more limitation, the element defined by the sentence "includes a . . . " does not exclude the existence of another identical element in the process, the method, or the device including the element. Herein, a "proximal" end or side refers to an end or side closer to an operator and farther away from a patient, while a "distal" end or side refers to an end or side farther away from the operator and closer to the patient.

In principle, the present invention seeks to provide an ultrasonic emulsifier which overcomes the problem of possible damage to other part of the eye during cataract surgery and consequent complications associated with conventional ultrasonic emulsifiers.

As shown in FIGS. 3 to 6, the present invention provides an ultrasonic emulsifier including an emulsifier body 201, on the emulsifier body 201 there are provided: an irrigation module 202 for dispensing a liquid into the eye, the liquid containing targeted microbubbles for acting on the crystalline lens of the eye; an ultrasound module 203 for producing ultrasound waves for acting on the eye and enabling the targeted microbubbles to act on the eye's lens; and a suction module (not labeled) for sucking the dispensed liquid and/or the broken-down lens from the eye.

Figure 7:
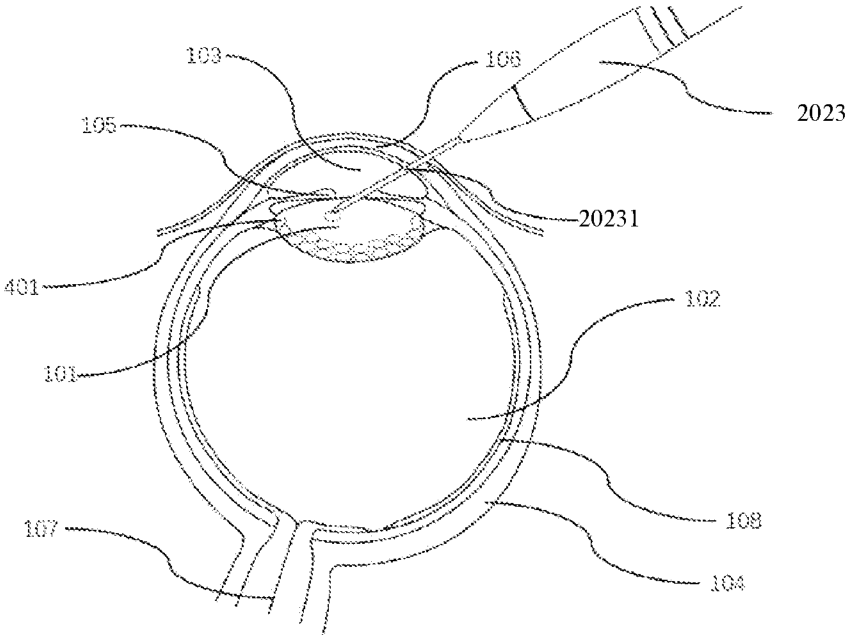
FIG. 7 schematically illustrates dispensing of targeted microbubbles during operation of an ultrasonic emulsifier according to an embodiment of the present invention.
Figure 8:
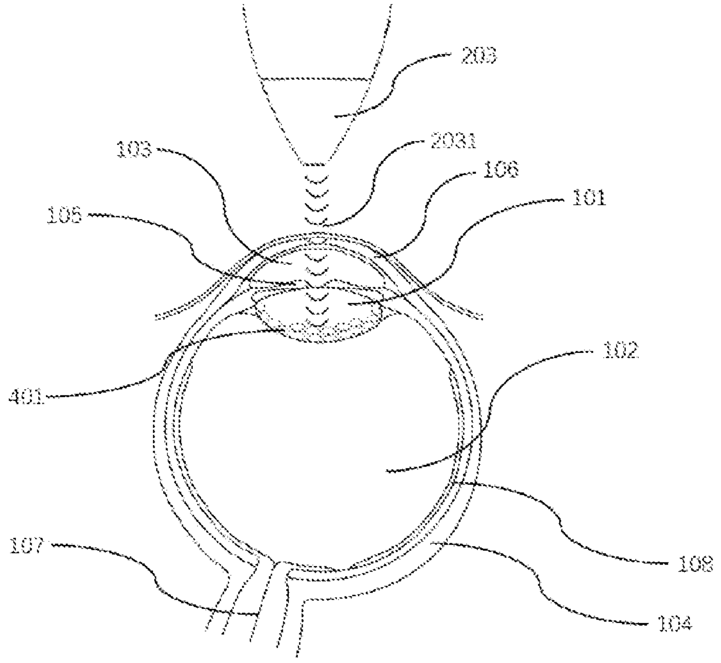
FIG. 8 schematically illustrates application of ultrasound waves during operation of an ultrasonic emulsifier according to an embodiment of the present invention.

According to the present invention, the irrigation module 202 is able to dispense targeted microbubbles into the eye. As shown in FIG. 7, after entering the eye, the targeted microbubbles 401 will preferentially bind to the diseased lens 101 due to their targeting properties. When ultrasound waves 2031 generated by the ultrasound module 203 acts on the eye, as shown in FIG. 8, the ultrasound waves 2031 can activate the targeted microbubbles 401 and induce cavitation therein, which results in the formation of cavitation bubbles (cavitation, or ultrasonic cavitation, is a dynamic process in which small vapor-filled cavities in a liquid vibrates and grows under the action of sound waves and collapses upon acoustic pressure reaching a certain level). Under the effect of cavitation, the targeted microbubbles 401 are excited by ultrasound waves 2031, and cavities/voids are formed in the targeted microbubbles 401. Those cavities/voids continue to vibrate under the action of ultrasound waves 2031 and, upon the energy reaching a certain level, compressed to completely collapse (i.e., they burst). When bursting, they can generate energy that is strong enough to break down the diseased cataract lens 101. Compared with directly breaking down the cataract lens 101, activating and inducing cavitation in the targeted microbubbles 401 requires less energy. Thus, compared with the traditional approach relying on direct ultrasonic cataract lens breakdown, the present invention can achieve lens breakdown using less ultrasound energy, resulting in less energy consumption and circumventing the use of excessive ultrasound energy which may cause damage to other parts of the eye and consequent complications. In addition, if the cataract nucleus is very hard, the irrigation and/or cavitation process of targeted microbubbles 401 can be repeated multiple times to totally break down the diseased lens 101, without significantly increasing the ultrasound energy used.

The present invention is not limited to any particular type of targeted microbubbles 401, as long as they can target and bind to the cataract lens. For example, they may target carboxyl groups (e.g., electrostatically, or by chelating) or less cells (e.g., by the monoclonal antibody HILE6). Since the targeted microbubbles 401 are not a focus of the present invention, further description thereof is omitted herein. After entering the eye 100, the targeted microbubbles 401 will be adsorbed around the lens 101 thanks to their targeting properties. This can maximize the utilization of cavitation energy and eventually reduce damage that may be caused to the surrounding tissue.

Optionally, the irrigation module 202 may include a gravitational irrigation module 2021, the gravitational irrigation module 2021 includes a support rod 20211 and an irrigation container (not labeled). The support rod 20211 is arranged on the emulsifier body 201 so as to extend outwardly from the emulsifier body. The irrigation container is arranged at a top end of the support rod 20211 located away from the emulsifier body. The irrigation container may be an infusion bag, which contains the liquid to be dispensed and is hung from the top end of the support rod 20211. Under the action of gravity, the liquid may be dispensed from the infusion bag in the form of drops. Preferably, a length of the support rod 20211 may be adjusted to change a flow speed and hence a flow rate of the liquid dispensed from the irrigation container. According to the present invention, the irrigation module 202 is not limited to employing the above-discussed gravitational irrigation module 2021, and any other means capable of dispensing the liquid into the eye can be suitably used without departing from the scope of the present invention. For example, an automated irrigation module 2022 may be adopted, which regulates the flow rate of the dispensed liquid based on pressure variation. For example, according to the present invention, in addition to dispensing targeted microbubbles to the eye, the irrigation module 202 may continuously supply a balanced salt solution such as physiological saline to the eye during cataract surgery to maintain normal intraocular pressure. In this embodiment, the gravitational irrigation module 2021 is able to adjust the flow rate of the liquid dispensed into the eye through changing the length of the support rod, and the automated irrigation module 2022 is able to automatically regulate the flow rate of the balanced salt solution disposed to the eye according to intraocular pressure variation and thereby maintain normal intraocular pressure. In practice, both the gravitational irrigation module 2021 and the automated irrigation module 2022 may be provided on the emulsifier body, and the surgeon may flexibly select either of them, as needed.

Preferably, according to the present invention, the irrigation module 202 further includes an irrigation handle 2023, the irrigation handle 2023 is used for dispensing, into the eye, the liquid containing the targeted microbubbles that target the eye's lens. According to this embodiment, another implementation of the irrigation module 202, i.e., the irrigation handle 2023 is further provided, the irrigation handle 2023 may be used separately to suck the targeted microbubbles and/or balanced salt solution therein and dispense it/them into the eye.

According to the present invention, the irrigation handle 2023 may also be used in combination with the gravitational irrigation module 2021 to better dispense the liquid into the eye. Specifically, the irrigation handle 2023 may be brought into communication with the gravitational irrigation module 2021. The gravitational irrigation module 2021 can be used to supply the balanced salt solution to the irrigation handle 2023, and the irrigation handle 2023 can be used to suck therein the targeted microbubbles that target and bind to the eye's lens and dispense the targeted microbubbles into the eye. For example, in this embodiment, the targeted microbubbles 401 may be stored in a bottle and may be sucked into a cavity defined in a handpiece body of the irrigation handle 2023 through a syringe needle 20231 provided at a distal end of the irrigation handle 2023. Subsequently, the targeted microbubbles 401 may be dispensed into the eye through the syringe needle 20231 at the distal end of the irrigation handle 2023. As shown in FIG. 7, this dispenses with the need to make a large incision in the cornea as in conventional phacoemulsification surgery, and allows a smaller incision to be made, resulting in significant improvements in safety, healing speed and robustness.

Figure 9:
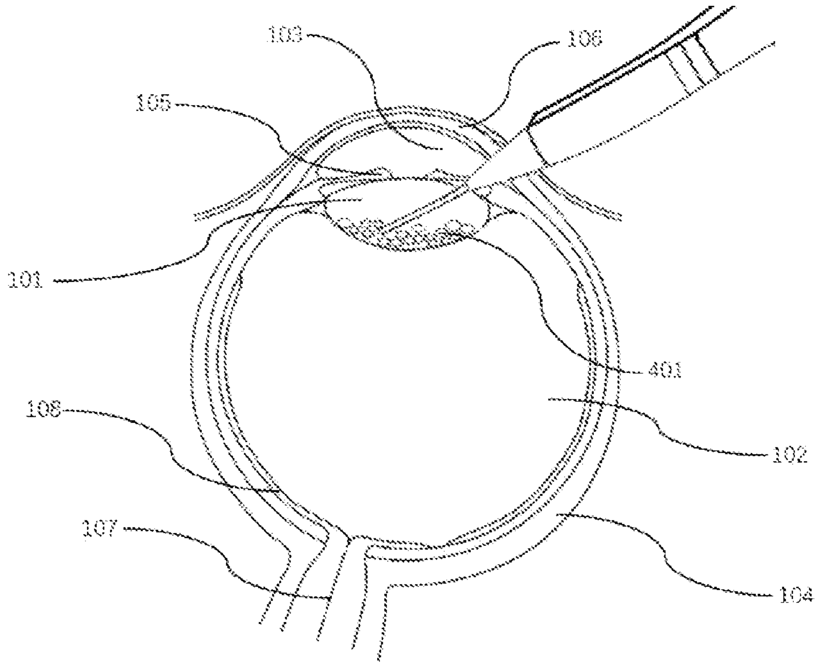
FIG. 9 schematically illustrates suction during operation of an ultrasonic emulsifier according to an embodiment of the present invention.

In another implementation of the present invention, the suction module may include a suction handle used to aspirate the dispensed liquid and/or the broken-down lens from the eye, as shown in FIG. 9.

Typically, for ease of operation, the irrigation handle and the suction handle may be combined into a single handpiece which may define two independent liquid passages: an irrigation passage and a suction passage. The gravitational irrigation module 202 may be used to supply the balanced salt solution to the irrigation passage of the handpiece, which may also serve for suction of the targeted microbubbles that target and bind to the eye's lens and dispensing thereof into the eye. The suction passage may serve for suction of the dispensed liquid and the broken-down lens from the eye. According to this embodiment, the handpiece can be used for both irrigation and suction, providing great ease of use.

The ultrasonic emulsifier may further include a fluid management module 204, the fluid management module 204 is connected to both the irrigation module 202 and the suction module and configured for flow rate control of the irrigation module 202 and the suction module.

Figure 10:
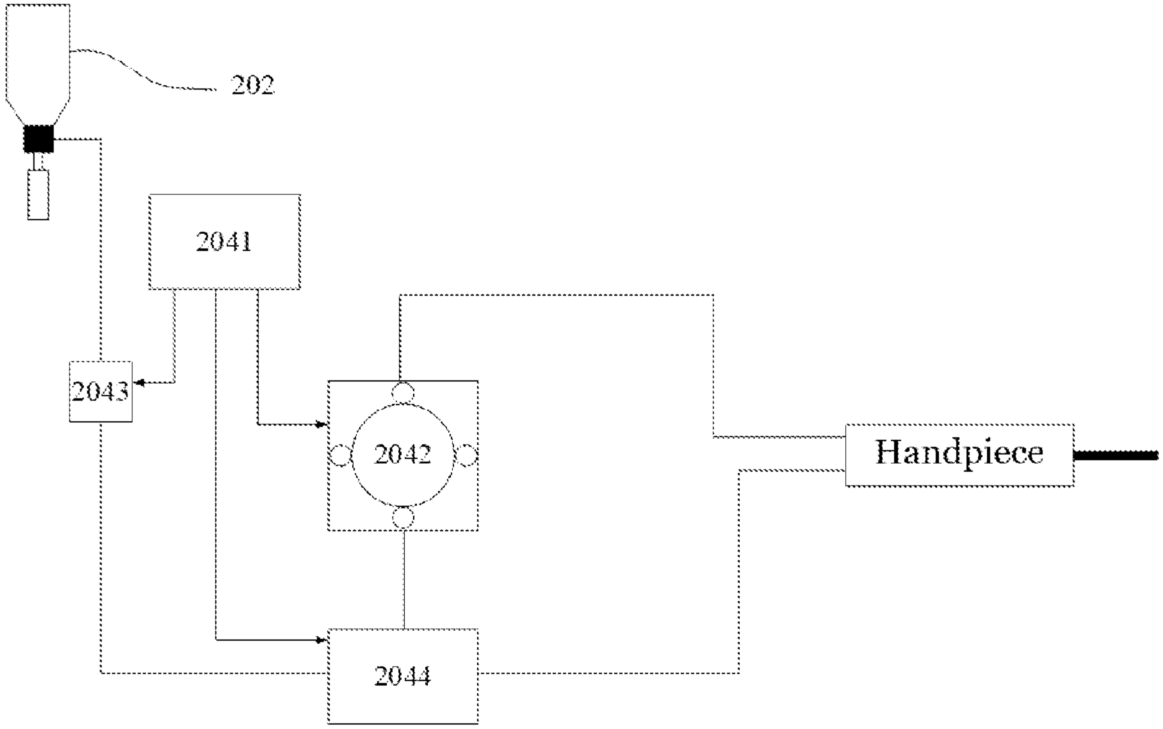
FIG. 10 schematically illustrates operation of a fluid management module according to an embodiment of the present invention.

Specifically, as shown in FIG. 10, the fluid management module 204 may include a fluid management module 2041, a control pump 2042, an irrigation valve 2043, a sensing module (not labeled) and a fluid collection cassette 2044. The irrigation module 202 communicates with the fluid collection cassette 2044 through the irrigation valve 2043, and the suction module communicates with the fluid collection cassette 2044 through the control pump 2042. The sensing module is used to collect pressure signals from the fluid collection cassette 2044, the irrigation module 202 and the suction module and provide the signals to the fluid management module 2041. The sensing module may include multiple sensors scatted in various pipes connecting, for example, the irrigation module 202, the suction module and the fluid collection cassette 2044. From the pressure signals received from the sensing module, the fluid management module 2041 determines an irrigation pressure of the irrigation module 202 and/or a suction pressure of the suction module and regulates operation of the control pump 2042 and the irrigation valve 2043 based on the irrigation pressure and/or the suction pressure. The control pump 2042 is configured to produce a negative pressure for adjusting a suction flow rate and pressure for the suction module, and the irrigation valve 2043 is configured to adjust an irrigation flow rate and pressure for the irrigation module 202. For example, the flow rate of the liquid dispensed from the irrigation module 202 may be varied by adjusting an opening size of the irrigation valve 2043.

The control pump 2042 may include a peristaltic pump, the peristaltic pump is composed of multiple pairs of symmetrical rollers arranged on a circular aluminum housing. Operation of the peristaltic pump may be controlled by a stepper motor. A pipe connecting the suction module and the fluid collection cassette 2044 may be clamped between the rollers of the peristaltic pump. In this way, the peristaltic pump is able to adjust a flow rate of a liquid in the pipe. Moreover, by adjusting operation of the peristaltic pump, a negative pressure can be produced to act on the suction module to enable it to aspirate a liquid and the broken-down lens from the eye into the fluid collection cassette through the pipe. Typically, there are two types of cortex in the broken-down lens: free fluffy cortical conglomerations within the anterior chamber; and normal cortex remaining attached to the posterior capsule. Often, the cortex can be peeled layer by layer like an onion, but there may be some hard layers which cannot be removed even at a maximum possible negative pressure that can be created by the peristaltic pump (i.e., the required negative pressure exceeds the capacity of the peristaltic pump). Accordingly, in addition to the peristaltic pump, a vacuum pump can be provided to add an option for the surgeon. For example, the vacuum pump may be connected in parallel to the peristaltic pump, and a pinch valve module may be additionally provided to enable selective connection of the suction module with a desired one of the peristaltic pump and the vacuum pump.

Further, the irrigation module 202 includes the gravitational irrigation module 2021 and the irrigation handle 2023, the gravitational irrigation module 2021 may be brought into communication with the irrigation handle 2023 through the irrigation valve 2043 and the fluid collection cassette 2044. The suction module includes the suction handle, the suction handle may be brought into communication with the fluid collection cassette 2044 through a pipe and the control pump 2042. In this way, the gravitational irrigation module 2021 can supply the balanced salt solution to the irrigation handle 2023 through the irrigation valve 2043 and the fluid collection cassette 2044, and the irrigation handle 2023 can be used to suck therein the targeted microbubbles that target and bind to the eye's lens and dispense the targeted microbubbles into the eye. The suction handle can be used to aspirate the dispensed liquid and the broken-down lens from the eye. Preferably, the irrigation handle 2023 and the suction handle are combined into a single handpiece defining an irrigation passage and a suction passage. In this case, the gravitational irrigation module 2021 may be brought into communication with the irrigation passage of the handpiece through the irrigation valve 2043 and the fluid collection cassette 2044. In addition to being adjusted by varying the opening size of the irrigation valve 2043, the irrigation flow rate can also be adjusted by manually changing a height of the irrigation container of the gravitational irrigation module 2021 based on an irrigation pressure signal received at the fluid management module 2041. The suction passage of the handpiece may be brought into communication with the fluid collection cassette through a pipe and the control pump.

Figure 11:
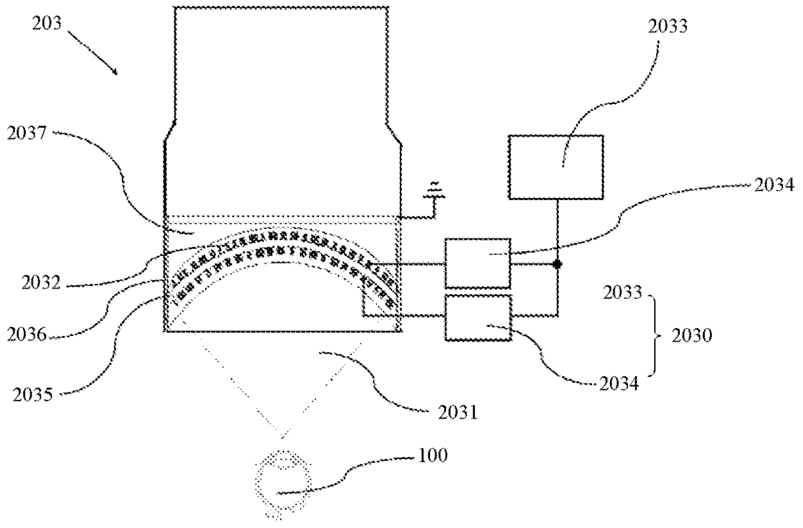
FIG. 11 is a schematic diagram showing the structure of an ultrasound module in an ultrasonic emulsifier according to an embodiment of the present invention.

In one implementation of the present invention, the ultrasound module 203 may include a focusing ultrasound transducer for delivering focused ultrasound energy to the eye. As shown in FIG. 11, according to the present invention, the focusing ultrasound transducer may particularly include multiple piezoelectric elements 2032, a carrier 2035 and an excitation component 2030. The excitation component 2030 is configured to excite the piezoelectric elements 2032 to cause them to emit ultrasound waves. The piezoelectric elements 2032 are arranged on the carrier 2035 into an arc so that the ultrasound waves emitted from the piezoelectric elements 2032 can converge to provide the focused ultrasound energy.

Optionally, the focusing ultrasound transducer may further includes a housing 2036 with an opening. The carrier 2035 is arc-shaped and mounted within the housing 2036. The opening of the arc-shaped carrier is aligned with the opening of the housing 2036. The piezoelectric elements 2032 are spaced apart across an inner surface and/or an outer surface of the arc-shaped carrier. Each piezoelectric element 2032 has one end electrically connected to the arc-shaped carrier, and the other ends of all the piezoelectric elements 2032 are connected together. Negative poles of the piezoelectric elements 2032 are grounded, and positive poles of the piezoelectric elements are electrically connected to the excitation component 2030. The excitation component 2030 may include a trigger module 2033 and a high-voltage pulse generator 2034. The positive poles of the piezoelectric elements 2032 are electrically connected to the high-voltage pulse generator 2034, and the trigger module 2033 is connected to the high-voltage pulse generator 2034. The trigger module 2033 can trigger generation of a high-frequency pulse signal by the high-voltage pulse generator 2034. Due to the inverse piezoelectric effect, when excited by the pulse signal, the piezoelectric elements 2032 will emit corresponding pulsed ultrasound waves. Because of the unique arrangement of the piezoelectric elements 2032 on the arc-shaped carrier 2035, the pulsed ultrasound waves that the piezoelectric elements 2032 emit will converge at a focus to form stronger pulsed ultrasound waves which are strong directionality and less divergence and can precisely act on the eye. That is, the ultrasound waves can accurately directed to the targeted microbubbles around the eye's lens, without causing damage to other eye tissue. Moreover, because the directionality of the focused pulsed ultrasound waves is higher than that of the conventional phacoemulsification approach, coupled with their use in combination with the targeted microbubbles, use of lower energy and a smaller incision is allowed, resulting in higher safety than the conventional approach.

The arc-shaped carrier may be a dome-shaped structure made of aluminum. Moreover, it may be integrally formed with the housing 2036. Additionally, the piezoelectric elements 2032 are preferred to be cylindrical in shape. A great number of such piezoelectric elements 2032 may be distributed across the inner and outer surfaces of the arc-shaped carrier. They may be randomly arranged lateral to one another according to the densest packing principle. Each piezoelectric element 2032 is fixed at its one end face to the inner or outer surface of the arc-shaped carrier, and is connected to the arc-shaped carrier by a wire. In a preferred implementation, the piezoelectric elements 2032 are fixed to the arc-shaped carrier with a conductive silver-containing epoxy adhesive. The electrical connection of the other end faces of the piezoelectric elements 2032 can be accomplished using silver-plated copper conductors. Those skilled in the art would appreciate that the carrier 2035 of the present invention may be made in any other suitable shape than arc-like. For example, it may have an irregular, hemispherical or another shape, as long as the piezoelectric elements 2032 can be arranged into an arc thereon so that ultrasound waves the piezoelectric elements 2032 produce can converge.

In implementations of this embodiment, the high-voltage pulse generator 2034 may consist of two parallel-connected high-voltage pulse generators, one of which contains a time function element, and the other is a regular high-voltage pulse generator. These two high-voltage pulse generator are connected in parallel and each electrically connected at one end to the trigger module 2033 and at the other end to a respective one of the piezoelectric elements 2032. That is to say, in the multiple piezoelectric elements 2032, the positive poles of two piezoelectric elements 2032 are connected respectively to the regular high-voltage pulse generator and the time function element-containing high-voltage pulse generator. Moreover, in order to ensure safety, the negative poles of two piezoelectric elements 2032 are always grounded and at a zero potential. The time function element-containing high-voltage pulse generator is configured so that the two high-voltage pulse generators can be triggered by the trigger module 2033 either simultaneously or independently. In this way, high-voltage pulses may be transmitted synchronously to the piezoelectric elements 2032, or with an adjustable time delay.

Further, in order to prevent leakage, gaps in the housing 2036 may be filled with an insulating filler 2037 that can withstand a high voltage.

Since the focusing ultrasound transducer is of well-known construction and not sought to be protected hereby, further detailed description of the structure thereof is omitted herein.

Figure 12:
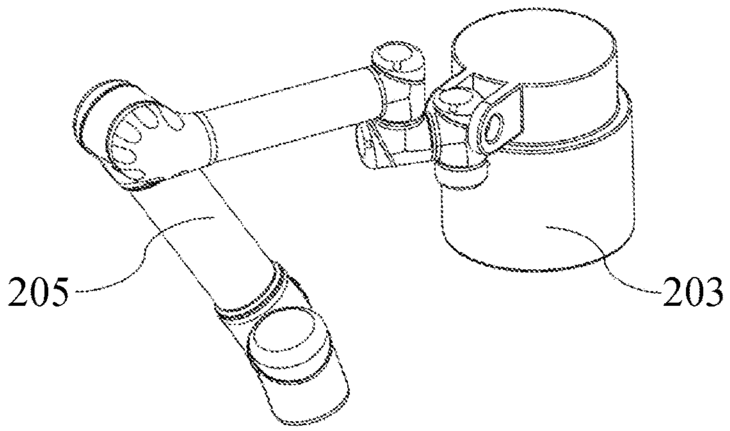
FIGS. 12 to 13 schematically illustrate coordinated motion of an ultrasound module and a robotic arm in an ultrasonic emulsifier according to an embodiment of the present invention.
Figure 13:
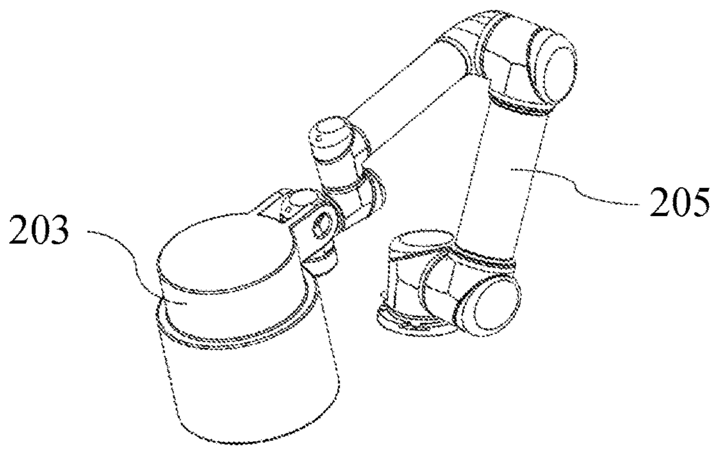

Preferably, as shown in FIGS. 12 to 13, the ultrasonic emulsifier of the present invention may include a robotic arm 205, the robotic arm 205 is connected to a housing of the ultrasound module 203. The robotic arm 205 is configured to move the ultrasound module 203 toward or away from the eye. The robotic arm 205 has multiple degrees of freedom and can be accurately placed under the control of system software at a position suitable for performing the surgical procedure on the patient's eye. Once the robotic arm 205 is positioned, the ultrasound module 203 coupled to one end of the robotic arm may precisely deliver focused ultrasound energy to the lesion site.

Operation of the ultrasonic emulsifier of the present invention will be detailed below. After the surgeon completes capsulorrhexis and hydrodissection/hydrodelineation, the targeted microbubbles are dispensed from the irrigation module to the patient's eye and target and bind to the diseased lens. In response to activation of the ultrasound module, focused pulsed ultrasound waves are delivered to the targeted microbubbles to activate them and induce cavitation therein, resulting in the formation of cavitation bubbles. Upon the energy reaching a certain level, the cavities/voids are compressed to completely collapse (i.e., they burst). When bursting, they can generate energy that is strong enough to break down the diseased cataract lens. Capsular rupture is a frequent complication of cataract surgery and mostly attributable to the use of a sharply tipped phacoemulsification needle. Therefore, training against capsular rupture forms an important part of surgical operation practice. In contrast, the external activation approach used in the present invention, which involves ultrasound focusing and cavitation, dispenses with the use of any sharp tool. Thus, this new cataract treatment is associated with a much lower risk of capsular rupture and/or damage to the other part of the eye (e.g., the cornea or the iris), compared with the conventional phacoemulsification method. Further, because of their targeting properties, the targeted microbubbles tend to be absorbed on the surface of the diseased lens, allowing the therapeutic energy to tend to be applied to the harder cataract rather than on other flexible tissue such as the lens capsule.

Figure 3:
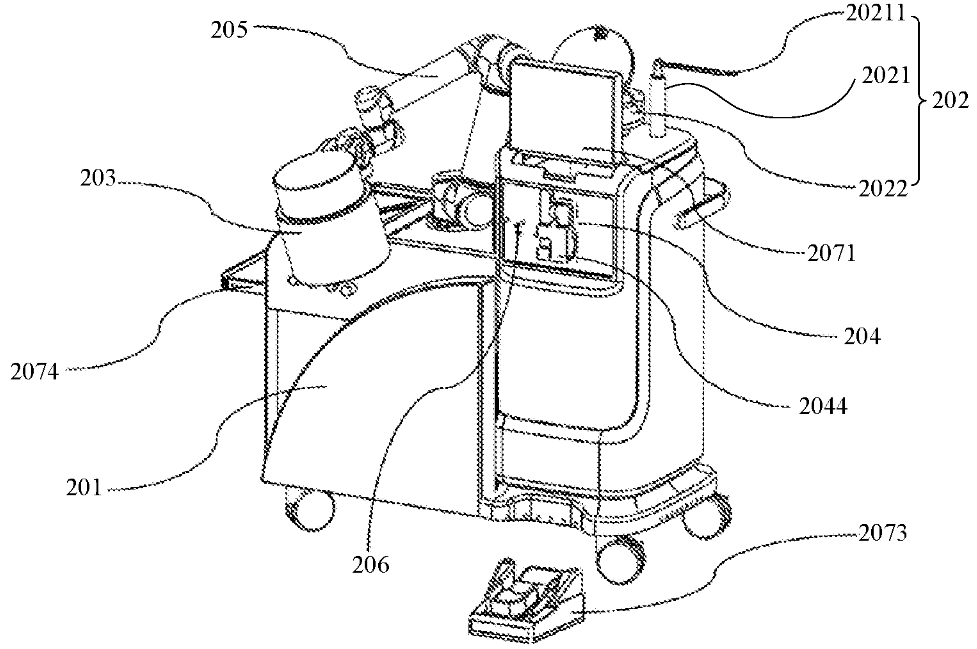
FIGS. 3 to 5 are different schematic views showing the structure of an ultrasonic emulsifier according to an embodiment of the present invention.
Figure 4:
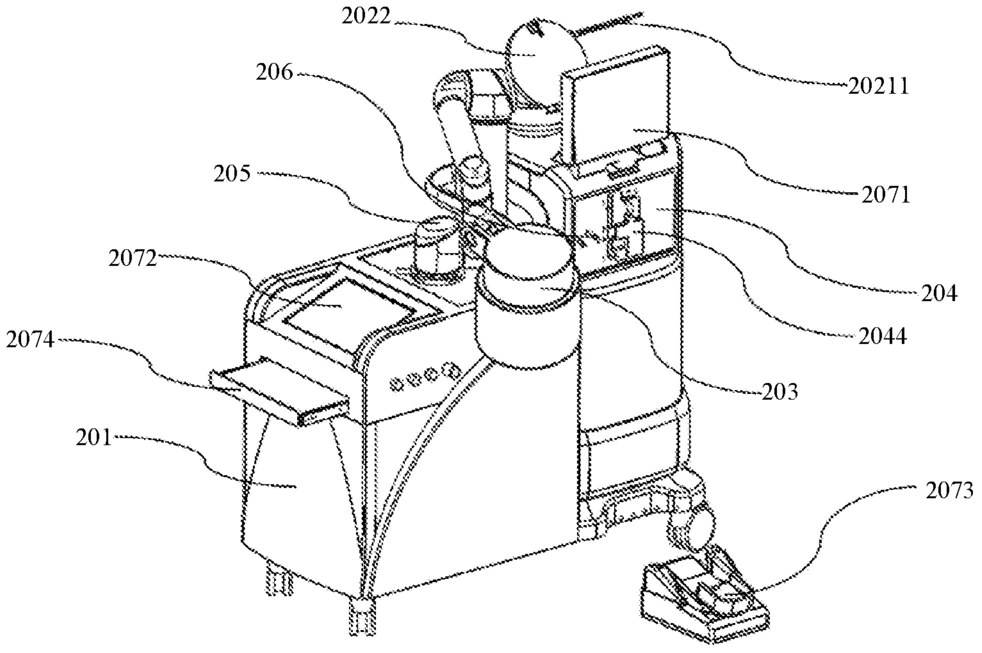
Figure 5:
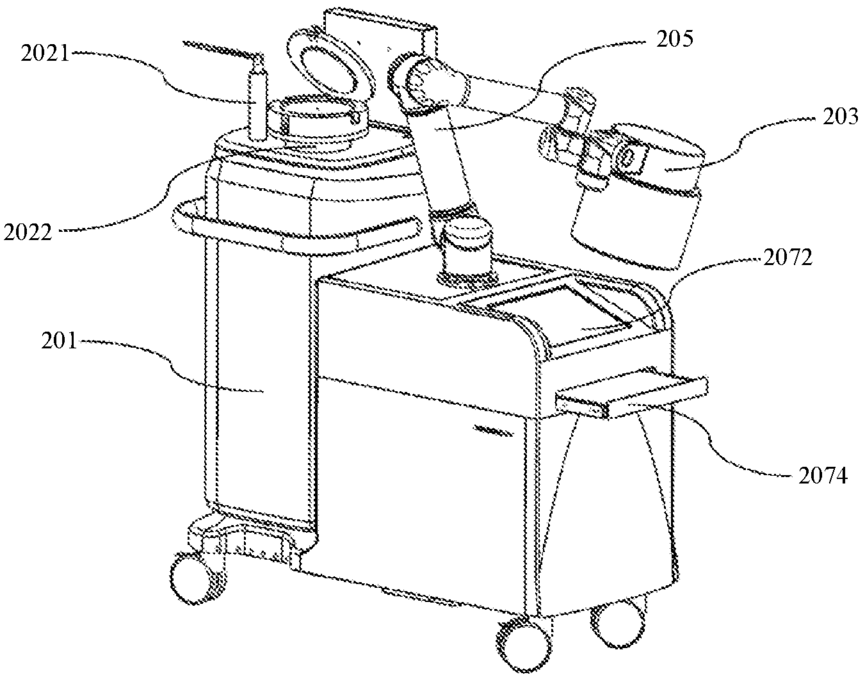
Figure 6:
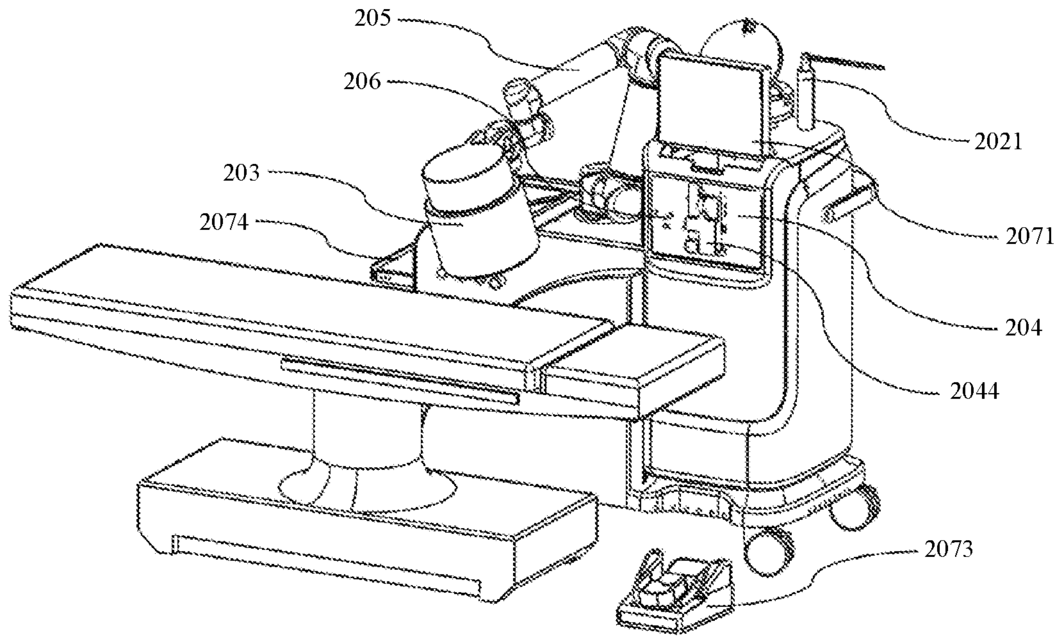
FIG. 6 is a schematic diagram showing the structure of an ultrasonic emulsifier in operation according to an embodiment of the present invention.

According to the present invention, other modules necessary for a surgical procedure may be further integrated in the ultrasonic emulsifier. As shown in FIGS. 3 to 5, for example, a port for connection with a vitrectomy module 206 may be integrated on the body of the ultrasonic emulsifier. The vitrectomy module 206 may be composed of a pneumatic handpiece, an air chamber, an air pump and a drive. It is used only if some events occur, such as capsular rupture and vitreous spillover, and is not used during normal cataract surgery.

In addition, as shown in FIGS. 3 to 5, the ultrasonic emulsifier may include a first display screen 2071, a second display screen 2072, a foot pedal 2073 and a surgical tray 2074. The first display screen 2071 is preferred to be a touch screen allowing the surgeon to choose or configure the system's functions. The second display screen 2072 is preferred to be a touch screen allowing a nurse to achieve positioning of the robotic arm 205 by issuing commands thereto. The surgical tray 2074 is used for placement of disposable consumables necessary for a surgical procedure. The foot pedal 2073 allows the surgeon to configure different surgical parameters based on his/her personal preferences or needs of the surgical procedure.

In summary, compared with the prior art, the ultrasonic emulsifier of the present invention has the advantages as follows:

It combines targeted microbubbles with ultrasonic cavitation by first dispensing the targeted microbubbles into a patient's eye and then activating the targeted microbubbles and inducing cavitation therein through the application of ultrasound energy. Energy generated from the cavitation breaks down the cataract nucleus in the diseased lens without causing damage to other tissue such as the lens capsule. Compared with direct breakdown of the cataract lens, less energy is required to activate the targeted microbubbles and induce cavitation therein. Therefore, compared with the conventional approach relying on direct ultrasonic breakdown of the cataract lens, the present invention can achieve lens breakdown using less ultrasound energy, resulting in less energy consumption and circumventing the use of excessive ultrasound energy which may cause damage to other parts of the eye and consequent complications of cataract surgery.

In addition, the ultrasound module of the present invention employs a focusing ultrasound transducer capable of producing pulsed ultrasound waves which can converge to gain the characteristics of strong directionality and less divergence. Compared with most of the conventional methods, which involve inserting an ultrasonic handpiece into the eye to apply ultrasonic energy thereto, the ultrasound module of the present invention entails a contactless approach allowing precise delivery of the focused ultrasound waves to the targeted microbubbles present around the eye's lens without inserting the ultrasound module into the eye, additionally reducing damage to other tissue of the eye. Moreover, because the directionality of the focused pulsed ultrasound waves is higher than that of the conventional phacoemulsification approach, coupled with their use in combination with the targeted microbubbles and the contactless approach, use of lower energy and a smaller incision is allowed, resulting in higher safety than the conventional methods.

The description presented above is merely that of a few preferred embodiments of the present invention and is not intended to limit the scope thereof in any sense. Any and all changes and modifications made by those of ordinary skill in the art based on the above teachings fall within the scope as defined in the appended claims. Apparently, those skilled in the art can make various modifications and variations to the present invention without departing from the spirit and scope thereof. Accordingly, the invention is intended to embrace all such modifications and variations if they fall within the scope of the appended claims and equivalents thereof.

What is claimed is:

1. An ultrasonic emulsifier, comprising an emulsifier body, the emulsifier body is provided with: an irrigation module configured to dispense a liquid into an eye, the liquid containing targeted microbubbles for acting on a lens of the eye; an ultrasound module configured to generate ultrasound waves for acting on the eye and enabling the targeted microbubbles to act on the lens of the eye; and a suction module configured to aspirate the dispensed liquid and/or a broken-down lens from the eye, wherein the ultrasound module comprises an ultrasound transducer, the ultrasound transducer configured to provide focused ultrasound energy for acting on the eye, wherein the ultrasound transducer comprises a plurality of piezoelectric elements, a carrier and an excitation component, the excitation component configured to excite the piezoelectric elements to generate the ultrasound waves, the piezoelectric elements arranged on the carrier into an are so as to converge the ultrasound waves generated by the plurality of piezoelectric elements to provide the focused ultrasound energy.

2. The ultrasonic emulsifier according to claim 1, wherein the irrigation module comprises a gravitational irrigation module, the gravitational irrigation module comprising a support rod and an irrigation container, the support rod disposed on the emulsifier body and extending outwardly from the emulsifier body, the irrigation container disposed at a top end of the support rod away from the emulsifier body.

3. The ultrasonic emulsifier according to claim 2, wherein the irrigation module further comprises an irrigation handle, the irrigation handle in communication with the gravitational irrigation module, wherein the gravitational irrigation module is configured to supply a balanced salt solution to the irrigation handle, and the irrigation handle is configured to suck the targeted microbubbles therein and dispense the targeted microbubbles into the eye.

4. The ultrasonic emulsifier according to claim 3, wherein the suction module comprises a suction handle, the suction handle configured to aspirate the dispensed liquid and/or the broken-down lens from the eye.

5. The ultrasonic emulsifier according to claim 4, wherein the irrigation handle and the suction handle are implemented as a single handpiece, the handpiece defining an irrigation passage and a suction passage, wherein the gravitational irrigation module is configured to supply the balanced salt solution to the irrigation passage of the handpiece; the irrigation passage of the handpiece is configured for suction of the targeted microbubbles that target and bind to the lens of the eye and for dispensing the targeted microbubbles into the eye; and the suction passage is configured for suction of the dispensed liquid and/or the broken-down lens from the eye.

6. The ultrasonic emulsifier according to claim 2, wherein the support rod has an adjustable length.

7. The ultrasonic emulsifier according to claim 1, further comprising a fluid management module, wherein the fluid management module is connected to both the irrigation module and the suction module, and wherein the fluid management module is configured for flow rate control of the irrigation module and the suction module.

8. The ultrasonic emulsifier according to claim 7, wherein the fluid management module comprises a control pump, an irrigation valve, a sensing module and a fluid collection cassette, the irrigation module communicating with the fluid collection cassette through the irrigation valve;

the suction module communicating with the fluid collection cassette through the control pump;

the sensing module configured to collect pressure signals from the fluid collection cassette, the irrigation module and the suction module and provide the pressure signals to the fluid management module, the fluid management module configured to determine an irrigation pressure of the irrigation module and/or a suction pressure of the suction module according to the pressure signals of the sensing module and regulate operation of the control pump and the irrigation valve based on the irrigation pressure and/or the suction pressure, the control pump configured to produce a negative pressure for adjusting a suction flow rate and the suction pressure of the suction module, the irrigation valve configured to adjust an irrigation flow rate and the irrigation pressure of the irrigation module.

9. The ultrasonic emulsifier according to claim 1, wherein the ultrasound transducer further comprises a housing with an opening, wherein the carrier is arc-shaped, the arc-shaped carrier is mounted in the housing, and an opening of the arc-shaped carrier is aligned with the opening of the housing; the piezoelectric elements are spaced apart across an inner surface and/or an outer surface of the arc-shaped carrier; and each of the piezoelectric elements is electrically connected at one end to the arc-shaped carrier and the other ends of the piezoelectric elements are electrically connected together.

10. The ultrasonic emulsifier according to claim 9, wherein negative poles of the piezoelectric elements are grounded and positive poles of the piezoelectric elements are electrically connected to the excitation component.

11. The ultrasonic emulsifier according to claim 10, wherein the excitation component comprises a trigger module and a high-voltage pulse generator, wherein the positive poles of the piezoelectric elements are electrically connected to the high-voltage pulse generator, and the trigger module is connected to the high-voltage pulse generator.

12. The ultrasonic emulsifier according to claim 9, further comprising a robotic arm connected to the housing of the ultrasound module, the robotic arm configured to move the ultrasound module toward or away from the eye.

* * * * *